(12) United States Patent
Zelechonok (10) Patent No.: US 10,371,141 B1
(45) Date of Patent: Aug. 6, 2019

(54) GRADIENT HIGH PRESSURE SYRINGE PUMP

(71) Applicant: Yury Zelechonok, Northbrook, IL (US)

(72) Inventor: Yury Zelechonok, Northbrook, IL (US)

( * ) Notice: Subject to any disclaimer, the term of this patent is extended or adjusted under 35 U.S.C. 154(b) by 339 days.

(21) Appl. No.: 15/219,084

(22) Filed: Jul. 25, 2016

(51) Int. Cl.
| | |
|---|---|
| *F04B 19/22* | (2006.01) |
| *F04B 49/22* | (2006.01) |
| *F04B 3/00* | (2006.01) |
| *F04B 19/00* | (2006.01) |
| *F04B 53/14* | (2006.01) |
| *F04B 13/02* | (2006.01) |
| *G01N 30/32* | (2006.01) |
| *G01N 30/38* | (2006.01) |

(52) U.S. Cl.
CPC ............... *F04B 49/22* (2013.01); *F04B 3/00* (2013.01); *F04B 13/02* (2013.01); *F04B 19/003* (2013.01); *F04B 19/22* (2013.01); *F04B 53/142* (2013.01); *G01N 2030/326* (2013.01); *G01N 2030/328* (2013.01); *G01N 2030/385* (2013.01)

(58) Field of Classification Search
CPC .......... F04B 3/00; F04B 19/003; F04B 19/22; F04B 49/22; F04B 53/142; F04B 13/02; G01N 2030/326; G01N 2030/328; G01N 2030/385
See application file for complete search history.

(56) References Cited

U.S. PATENT DOCUMENTS

| | | | | |
|---|---|---|---|---|
| 1,950,063 A | * | 3/1934 | Pescara .................... | F02B 71/04 123/46 R |
| 2,497,300 A | * | 2/1950 | Elliott .................... | F04B 53/142 417/386 |
| 2,572,977 A | * | 10/1951 | Bodine, Jr. ........... | F04B 19/003 417/211 |
| 2,807,215 A | * | 9/1957 | Hawxhurst ........... | F04B 43/107 417/383 |
| 2,936,712 A | * | 5/1960 | Van Gerpen .......... | F04B 1/0408 417/386 |
| 3,215,080 A | * | 11/1965 | Springer ................ | F02M 43/02 417/382 |
| 3,314,594 A | * | 4/1967 | Rietdijk ................ | F04B 35/008 417/244 |
| 3,485,176 A | * | 12/1969 | Telford .................... | B08B 3/026 122/448.1 |
| 3,847,507 A | | 11/1974 | Sakiyama et al. | |

(Continued)

*Primary Examiner* — Christopher S Bobish
(74) *Attorney, Agent, or Firm* — John C. Shepard (57) ABSTRACT

A gradient high pressure syringe pump usable in a high pressure liquid chromatography system includes a housing defining an internal cavity, a drive piston, and a floating piston unconnected from the drive piston dividing the internal cavity into first and second pumping chambers. Each pumping chamber has an intake inlet with an upstream no-return valve communicating with a source of fluid and a discharge outlet communicating with an inlet of a downstream control valve. The control valve is operable to selectively direct fluid from either of the upstream pumping chambers downstream. In one embodiment, the first pumping chamber defines a cylinder section for the drive piston having an internal diameter smaller than the cylinder section defined by the second pumping chamber for the floating piston. The drive piston is moved linearly between suction and discharge strokes by an attached screw operatively coupled with a controllable stepper motor.

17 Claims, 7 Drawing Sheets

(56) References Cited

U.S. PATENT DOCUMENTS

| | | | | |
|---|---|---|---|---|
| 3,861,222 | A | * | 1/1975 | Braun .................... F04B 25/00 |
| | | | | 74/44 |
| 4,406,158 | A | | 9/1983 | Allington |
| 4,412,552 | A | * | 11/1983 | Kolbanovsky ........... B01J 3/002 |
| | | | | 137/14 |
| 4,939,943 | A | | 7/1990 | Strohmeier |
| 4,980,296 | A | | 12/1990 | Trisciani et al. |
| 5,217,590 | A | | 6/1993 | Lauer et al. |
| 5,656,034 | A | | 8/1997 | Kochersperger et al. |
| 5,920,006 | A | | 7/1999 | Zelechonok |
| 6,257,052 | B1 | | 7/2001 | Zelechonok |
| 6,267,086 | B1 | * | 7/2001 | Dingle ................... F02M 43/00 |
| | | | | 123/25 C |
| 7,827,961 | B2 | * | 11/2010 | Cooke .................... F02M 43/02 |
| | | | | 123/446 |
| 9,109,587 | B2 | * | 8/2015 | Adler ........................ F04B 3/00 |
| 2012/0282118 | A1 | * | 11/2012 | Suzuki ..................... A61M 1/14 |
| | | | | 417/254 |

\* cited by examiner

GRADIENT HIGH PRESSURE SYRINGE PUMP

DESCRIPTION

BACKGROUND OF THE INVENTION

Technical Field

The present invention relates to a high pressure syringe pump and, more particularly, to a pump for chromatography which is capable of generating controllable binary gradient flow of liquid at high pressure suitable for high pressure liquid chromatography.

Background Art

High pressure liquid chromatography (HPLC) systems include chromatography columns and often various other fluidic devices or components, including, but not limited to pumps, injector, detectors, and the like, which are connected together by capillary tubes providing fluid communication.

These HPLC systems operate at pressures of 5,000 PSI and higher. To generate these pressures, high pressure pumps providing constant and controllable flow are employed. There are two main types of pumps available for chromatography. One is a reciprocating type, and the other is a syringe type.

Reciprocating pumps are more common since they can operate continuously and do not have a specific liquid volume capacity. In contrast, syringe pumps have limited liquid volume capacity requiring a refill cycle during which they are periodically reloaded. This interrupts liquid flow and the overall chromatography process. If the volume of the syringe pump were increased to a capacity level allowing for a day of continuous operation, the pump becomes too heavy and bulky to make it practical for use.

A big advantage of syringe pumps is that they produce pulse free flow. The flow from reciprocating pumps needs to be buffered using additional devices to minimize pulsations. Even when buffering the pulsations in fluid discharged from reciprocating pumps can be seen in some high sensitivity applications.

One approach to minimize the problem of syringe pump refill interruption is to make the volume of the syringe sufficient only for one chromatography analysis. In this case, a refill can be done prior to each analysis cycle and the size of the syringe can therefore be made relatively small. With this approach, the interruption of the chromatography process can be avoided during chromatography analysis.

Improvement in syringe pump size can be made if only small, narrow-sized columns are used for analysis. (G. I. Baram et al., "New Potentialities of HPLC in Pharmacopoeian Analysis," *Bulletin of Experimental Biology and Medicine*, January 2003, Volume 135, Issue 1, pp. 62-66). In this type of application, a volume of 1-5 mL of solvent can be used for a single analysis. If a syringe pump is designed for just 5 mL of solvent capacity, the size, weight, and refill time will be within convenient lab operational settings. Portable HPLC instruments can even be built based on such settings.

A significant number of chromatography methods require a gradient mode of solvent delivery. To generate gradient flow with constantly changing composition of the mobile phase (MP), two syringe pumps are usually needed. They are connected in parallel on the high pressure end through a flow mixer. A multi-syringe system means that there is increased size, weight, and control complexity, which can be problematic for portable applications. Examples of single and multi-syringe pump systems are shown in Kochersperger et al. U.S. Pat. No. 5,656,034, which issued Aug. 12, 1997.

It is noted that having two high pressure pumps working in parallel also requires twice the power for mechanical drivers compared to a single motor operation. This can be an added problem for portable systems. Another disadvantage of a dual pump system is the cost of the components, double compared to that of a single pump system.

BRIEF SUMMARY OF THE INVENTION

The present invention is directed to overcoming one or more of the problems as set forth above.

The primary object of the present invention to provide a chromatography syringe pump of small size and weight suitable for portable instrumentation applications.

It is a further object of the present invention to provide a chromatography syringe pump with a simple control suitable for isocratic as well as gradient modes of operation.

It is an additional object of the present invention to provide a chromatography gradient syringe pump with only one driver motor so that the power requirement is half that of a dual pump/motor design.

In one aspect of the present invention, a chromatography gradient syringe pump is provided that is less expensive to build and has a smaller number of components relative to a gradient dual-pump design.

BRIEF DESCRIPTION OF THE SEVERAL VIEWS OF THE DRAWINGS

The details of construction and operation of the invention are more fully described with reference to the accompanying drawings which form a part hereof and in which like reference numerals refer to like parts throughout.

In the drawings.

All figures are drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood.

DETAILED DESCRIPTION OF THE PREFERRED EMBODIMENTS

While the present invention is susceptible of embodiment in many different forms, there are shown in the drawings and will be described herein in detail specific embodiments thereof with the understanding that the present disclosure is to be considered as an exemplification of the principles of the invention and is not intended to limit the invention to the specific embodiments illustrated.

This invention generally relates to high pressure liquid chromatography ("HPLC") and to ultra high pressure liquid chromatography ("UHPLC"), but is not limited thereto and may be employed in other fields as well. An HPLC system may include an analytic chromatography column and various fluidic devices or components, including, but not limited to a pump, injector, detector, and the like, which are connected together by capillary tubes providing fluid communication.

Figure 1:
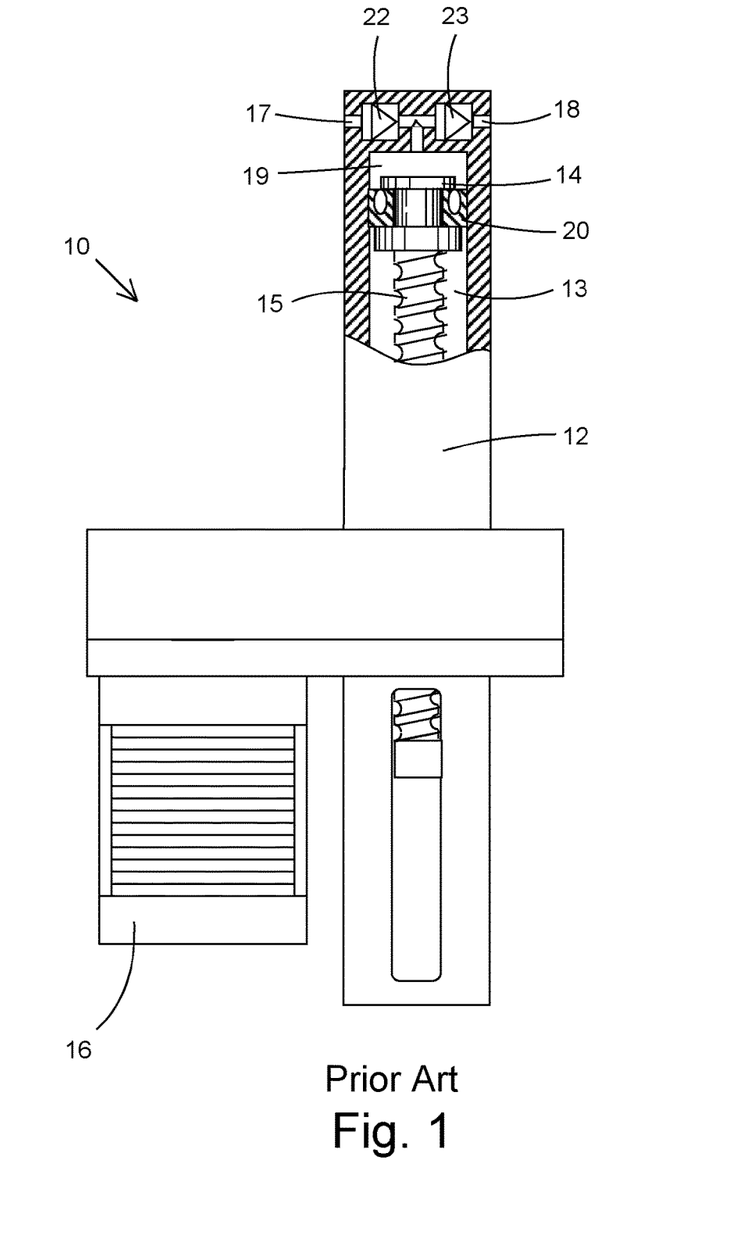
FIG. 1 is an elevational view partially broken away of a prior art small volume syringe pump that can be used for isocratic high pressure chromatography applications.
Figure 2:
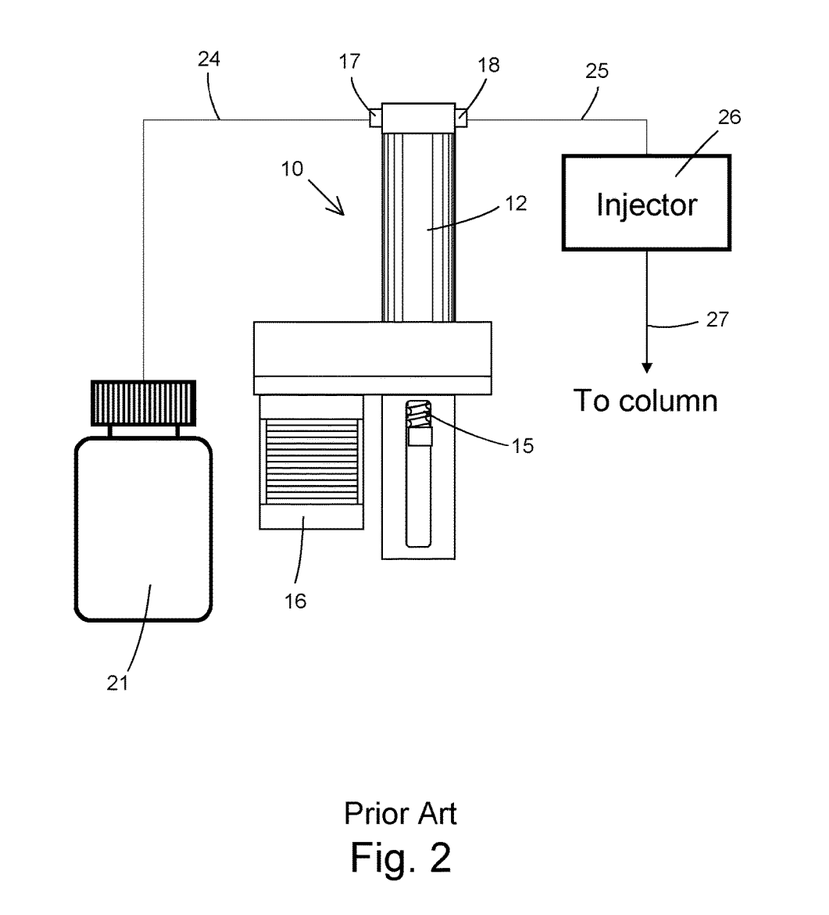
FIG. 2 is a schematic view of the prior art pump shown in FIG. 1 employed in a chromatographic system connected for isocratic chromatography analysis.
Figure 3:
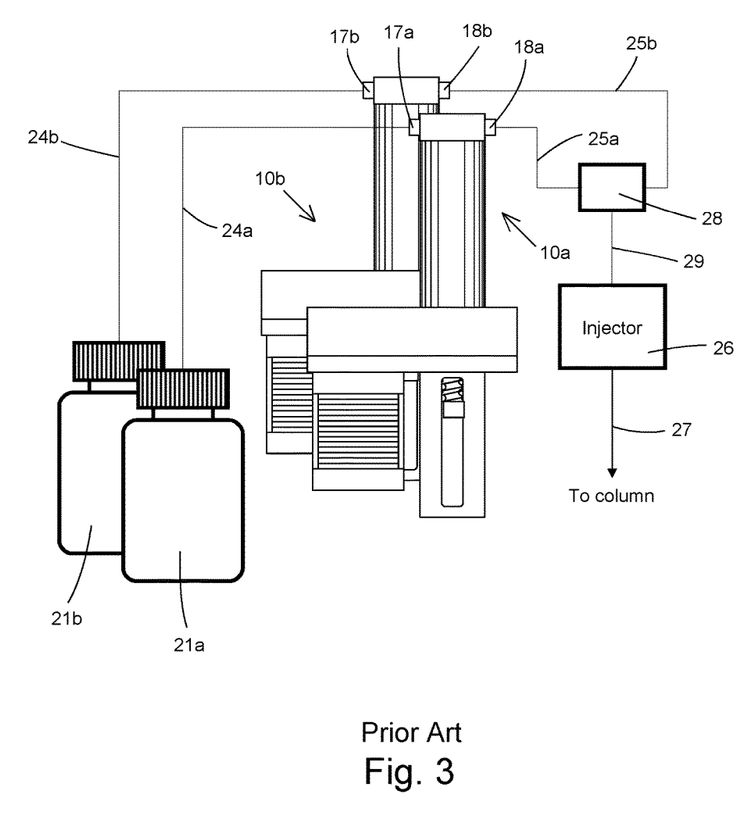
FIG. 3 is a schematic view of two prior art pumps shown in FIG. 1 connected for gradient chromatography analysis between a pair of upstream reservoirs and a downstream mixer discharging to an injector and column.

In FIGS. 1-3, a typical prior art HPLC syringe pump, generally designated 10, is shown. The positive displacement piston pump 10 includes a barrel housing 12 defining an internal cylinder 13, s piston 14 slidably mounted within the cylinder 13, a screw shaft 15, and a stepper motor 16 for moving the screw shaft 15 and the attached piston 14 linearly along the pump axis. At the head end of the housing are an inlet port 17 and an outlet port 18 communicating with the pumping chamber 19. An annular seal 20 is mounted in a groove formed in the piston external wall and sealingly engages the cylinder internal wall. When the screw shaft 15 retracts the piston 14 from the chamber 19, fluid is drawn into the chamber 19 from an external upstream supply 21 through the inlet port 17. When the screw shaft 15 drives the piston 14 into the chamber 19, fluid is discharged from the outlet port 18 downstream. A check valve 22 at the inlet port 17 prevents downstream fluid flow from the chamber 19. Similarly, a check valve 23 at the outlet port 18 prevents upstream fluid flow into the chamber 19.

In FIG. 2, the prior art pump 10 of FIG. 1 is schematically shown employed in an HPLC system configured for isocratic chromatography analysis. Solvent (sometimes referred to as eluent or mobile phase) stored in an upstream container 21 is drawn into pump intake inlet port 17 through inlet tubing line 24 and delivered from the pump discharge outlet port 18 through outlet tubing line 25 downstream to the inlet of a sample injector 26. Mobile phase, i.e., the mixture of solvent and sample, exits the injector 26 and flows downstream through line 27 to an analytic column.

In FIG. 3, a pair of prior art pumps 10a and 10b are employed in an HPLC system configured for gradient chromatography analysis. The two pump inlets 17a and 17b respectively communicate with two upstream solvent supply containers 21a and 21b via inlet tubing lines 24a and 24b. Solvent is discharged from the pump outlets 18a and 18b through outlet tubing lines 25a and 25b to the respective inlets of mixer 28. Solvent is then communicated through an outlet tubing line 29 downstream to the inlet of the sample injector 26. The mixture of solvent and sample exits the injector 26 and flows downstream via tubing line 27 to the analytic column.

Figure 4:
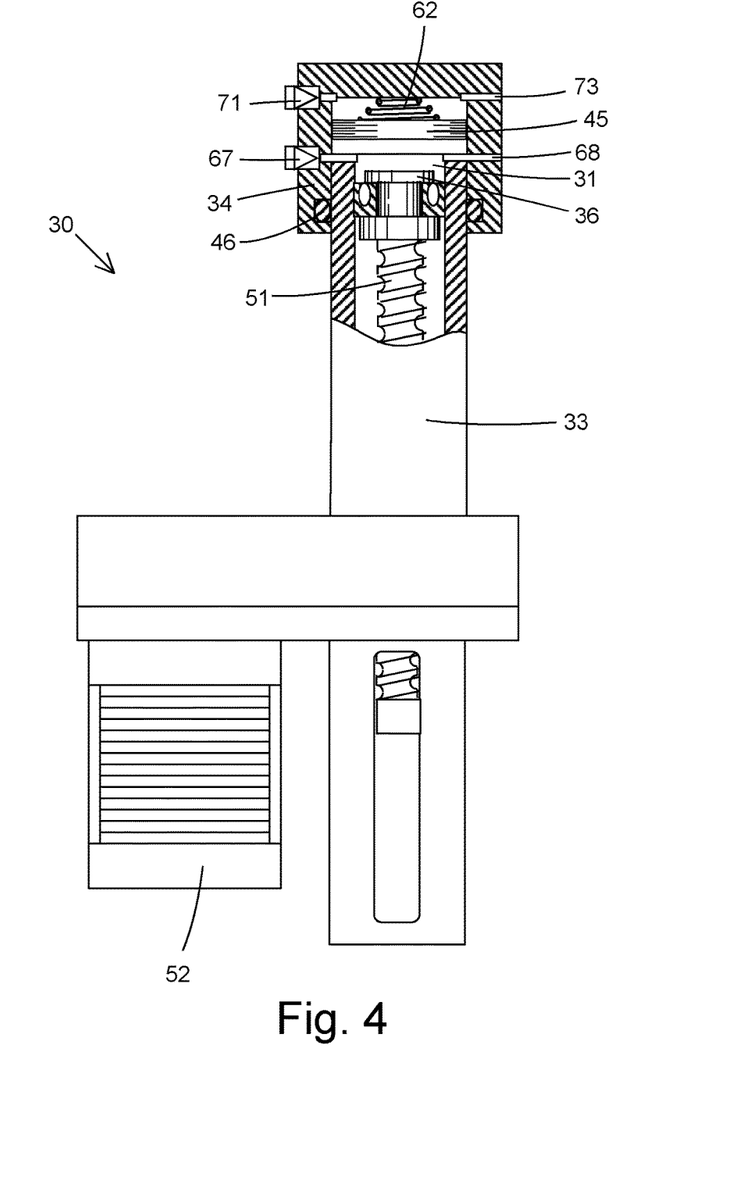
FIG. 4 is an elevational view partially broken away of a small volume syringe gradient pump employing the principles of the invention that can be used for gradient high pressure chromatography applications.
Figure 5:
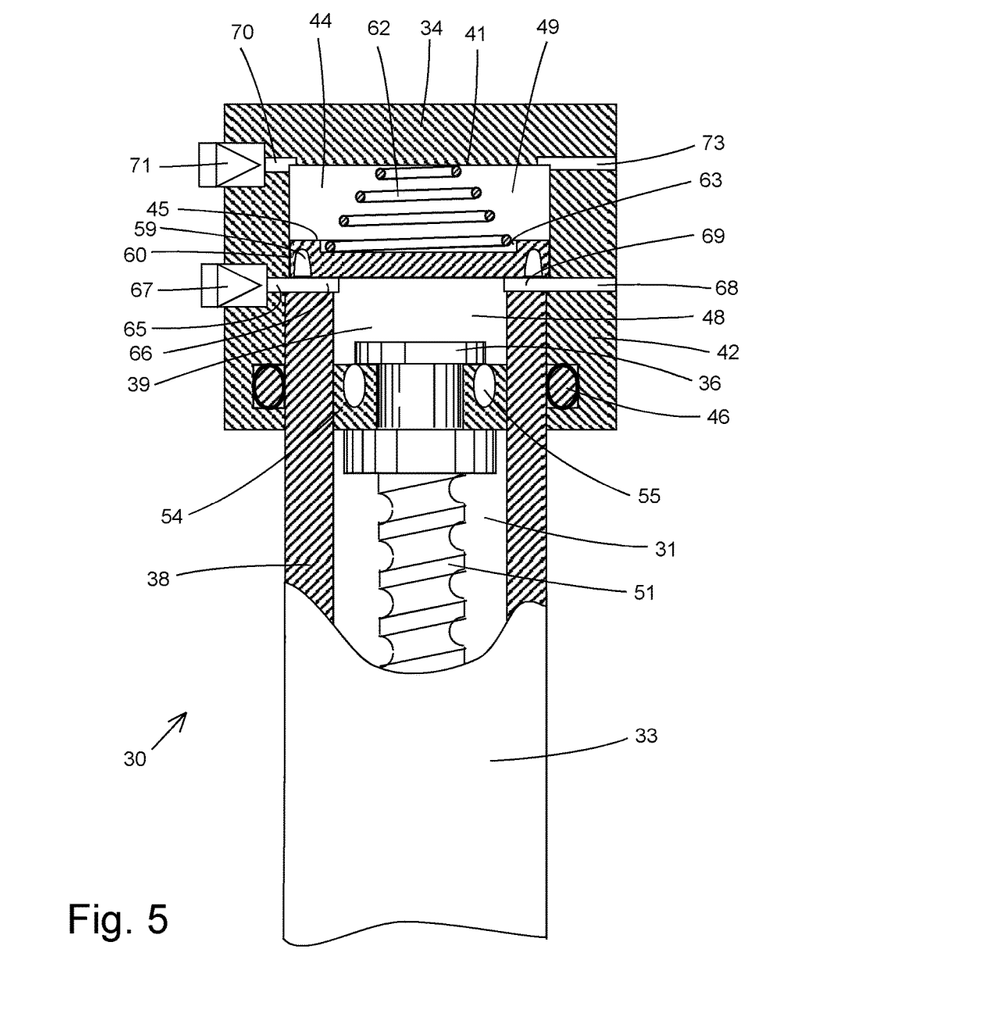
FIG. 5 is an enlarged, partial cross-sectional view of the syringe gradient pump shown in FIG. 4 with the floating piston in an inward position.
Figure 6:
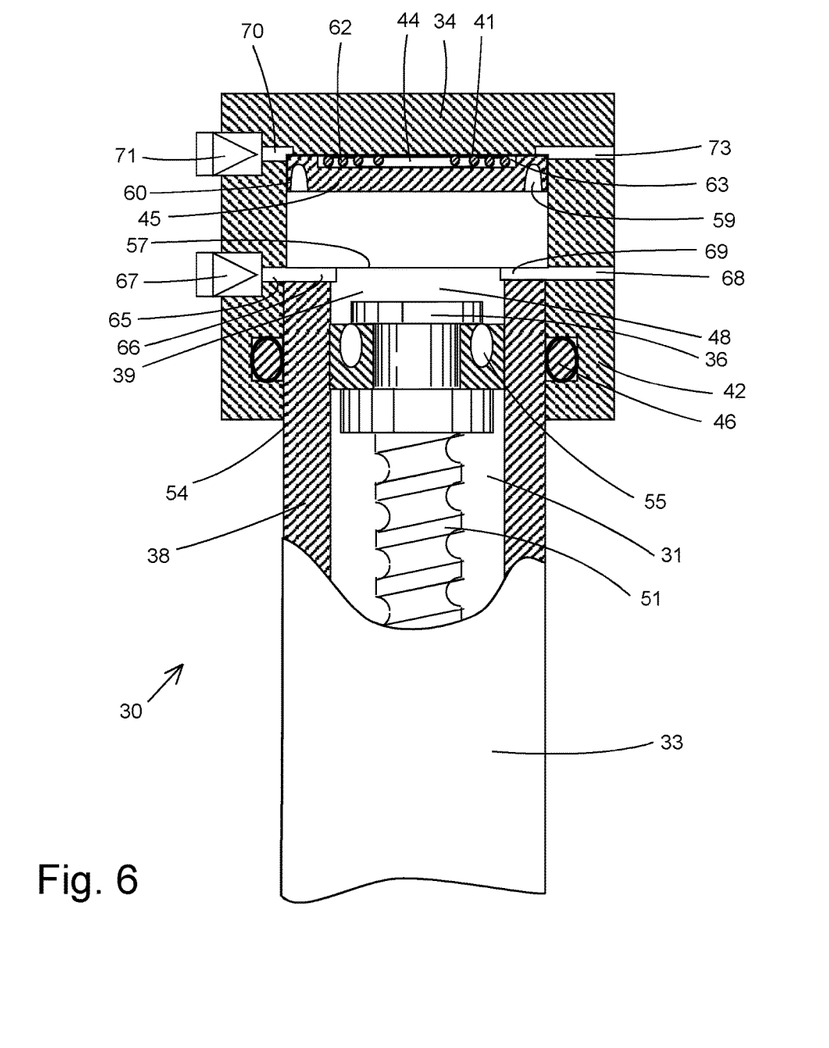
FIG. 6 is an enlarged, partial cross-sectional view of the syringe gradient pump shown in FIG. 4 with the floating piston in an outward position; and, FIG. 7 is a schematic view of the syringe gradient pump shown in FIG. 4 connected for gradient chromatography analysis between a pair of upstream reservoirs and a downstream valve controlling fluid flow to an injector and column.

In FIGS. 4-6, an embodiment of a gradient pump constructed in accordance with the present invention is shown. The gradient pump, generally designated 30, has an internal cavity 31 of variable volume enclosed by a barrel, or housing 33, by an endcap 34 at the head end of the housing 33, and by the head of a reciprocable drive piston 36 at the foot end. The housing 33 has a cylindrical side wall 38 defining a first cylinder section 39 within which the drive piston 36 is slidably mounted for linear movement along the pump axis between inward retracted position and an outward extended position. The endcap 34 has a transverse planar end wall 41 and an annular side wall 42 defining a second cylinder section 44 within which a separating floating piston 45, or plunger, is slidably mounted for reciprocating axial movement. The endcap 34 is fixed to the head end of the barrel by suitable means, preferably one that allows for removal of the endcap for pump maintenance. A seal between the housing and the endcap, which are made of stainless steel, or any other suitable material, is maintained by an annular O-ring 46 residing within an annular groove formed in the endcap side wall 42.

The floating piston 45 unconnected with the drive piston 36 divides the internal cavity 31 within the housing body into separate inner and outer internal pumping chambers 48 and 49, respectively. As will become more apparent hereafter, the inner chamber 48 includes the first cylinder section 39 and a varying-volume inner portion of the second cylinder section 44, while the outer chamber 49 includes a varying-volume outer portion of the second cylinder section 44.

The first and second cylinder sections 39 and 44 lie along a common longitudinal center axis extending through the housing barrel 33 and endcap 34. A screw shaft 51 is mounted along the center axis by suitable means within the housing 33 and is coupled with a stepper motor 52 for moving the screw shaft 15 and the attached piston 36 linearly along the pump axis within the first cylinder section 39 between a retracted position (FIG. 5) and an extended position (FIG. 6). The direction and speed of the stepper motor 52 may be controlled electronically or manually or by other suitable means.

The drive piston 36 may be extended toward the pump head end in a forward discharge stroke to reduce the volume of the first chamber 48 or retracted away from the pump head in a rearward suction stroke to increase the volume of the first chamber 48. A resilient piston seal 54 is positioned in an annular groove defined in the outer circumference of the piston. Within a circular channel formed in the piston seal is an energized spring 55 that imparts a force enabling initial contact with the interior wall of the first cylinder section 39.

The floating piston 45 is movable between a first position against the head edge 57 of the housing 33 (FIG. 5), which acts an abutment limiting inward axial movement of the floating piston 45, and a second position against the internal surface of the planar end wall 41 of the endcap 34 (FIG. 6), which acts as an abutment limiting outward axial movement of the floating piston 45. A groove 59 is formed in the bottom surface of the floating piston 45 adjacent the edge to form a lip or peripheral skirt 60 that sealingly slides along the internal surface of the side wall 38 of the endcap 34. The floating piston 45 can be made of soft chemically inert plastic, such as polytetrafluoroethylene (PTFE) or polyethylene.

A tapered constant force return spring 62 is located within the outer chamber 49 between the end wall 41 of the endcap 34 and the top of the floating piston 45 to resiliently bias the floating piston 45 downward toward the inner chamber 48. Formed in the top of the floating piston 45 facing the pumping chamber 49 is a cylindrical recess 63 that maintains the spring 62 in position by circumscribing the large outer turn of the spring 62. When the floating piston 45 is forced against the head end of the endcap 34, the spring 62 will lie entirely with the recess 63 as seen in FIG. 6. This allows upper cylinder volume to be minimized. The spring 62 need only apply a small loading force of approximately 2-10 pounds.

An intake inlet port 65 communicating with the inner chamber 48 is defined by an aperture in the side wall 42 of the endcap 34 intersecting an internal arcuate slot 66 defined in the outer edge 57 of the housing wall 38. A one-way check valve 67, or no-return valve, shown schematically upstream of the inlet port 65 prevents backflow from exiting from the inner chamber 48. A discharge outlet port 68 from the inner chamber 48 is defined by an aperture in the side wall 42 of the endcap 34 intersecting an internal arcuate slot 69 defined in the outer edge 57 of the housing wall 38 opposite the inlet port 65.

An intake inlet port 70 to the outer chamber 49 is defined by an aperture in the side wall 42 of the endcap 34. A one-way check valve 71, or no-return valve, shown schematically upstream of the inlet port 70 prevents backflow from exiting the outer chamber 49. A discharge outlet port 73 from the outer chamber 49 is defined by an aperture in the side wall 42 of the endcap 34 opposite the inlet port 70.

In FIG. 5, the drive piston 36 is positioned inwardly from the head end of the cylinder barrel 33 and the floating piston 45 is biased to an axially inward position into abutment with the head end of the cylinder barrel 33. In FIG. 6, the drive piston 36 is moved toward the head end of the cylinder barrel 33 away from the outer end of the barrel and the floating piston 45 under fluid pressure is moved to an axially outward position into abutment with the end wall 41 of the endcap 34.

Figure 7:
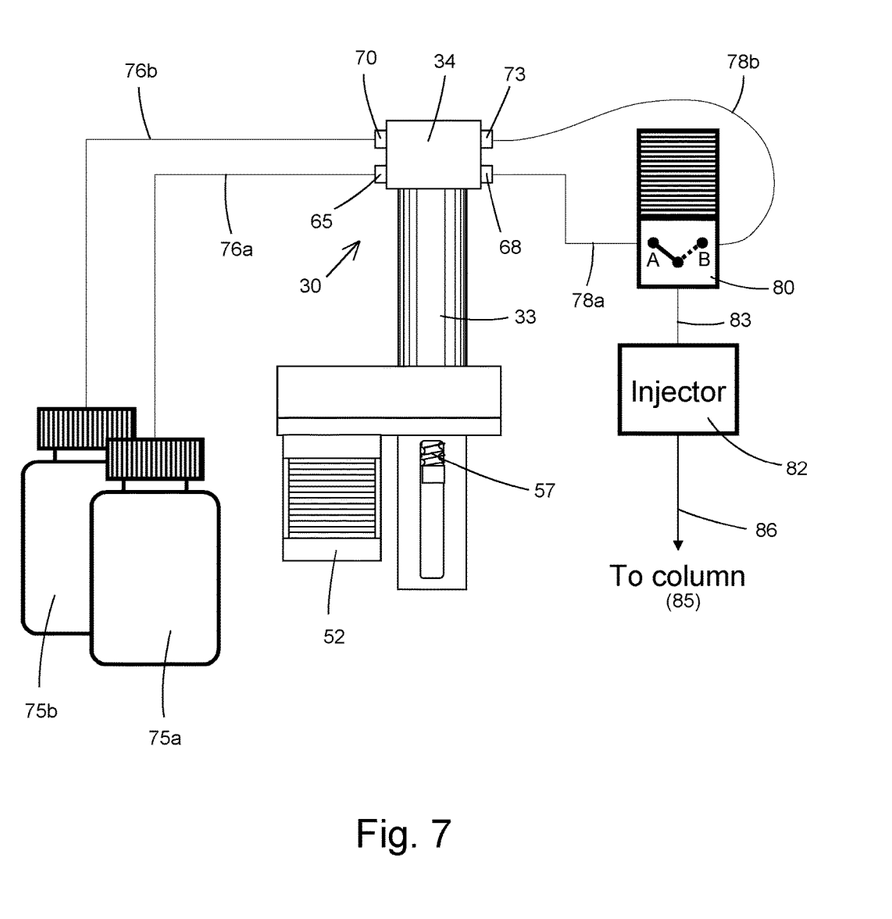

In FIG. 7, the gradient pump 30 is schematically shown employed in an HPLC system. A pair of upstream reservoirs 25a and 25b are connected to respective inlet ports 65 and 70 of the pump 30 by inlet tubing lines 76a and 76b. The pump outlets 68 and 73 are connected to the respective valve inlets by tubing lines 78a and 78b. Downstream of the pump 30 is a 3-port, 2-position, solenoid-operated, control valve 80 that may be selectively operated to direct fluid entering one of its inlets to its outlet. In valve position A as shown in FIG. 7, solvent from container 75a discharged from the pump inner outlet 68 is directed to the sample injector 82 through connecting tube 83. In valve position B, solvent from container 75b discharged from the pump outer outlet 73 is directed to the sample injector 82. Thereafter, solvent and sample flows downstream to the analytical column 85 through outlet tubing line 86.

A typical diameter for the drive piston 36 is 10 millimeters and, for the floating piston 45, 10-250 millimeters. Preferably, the diameter of the floating piston 45 is 2 to 3 times the diameter of the drive piston 36. The diameter of the outer cylinder section 44 is larger than the cylinder of section 39 still maintaining comparable volume capacities. This allows the use of a smaller spring with short travel. The typical overall distance traveled by the drive piston 36 is approximately 50 millimeters.

In operation, when the control valve 80 is moved to position A, axial movement of the drive piston 36 during its discharge stroke outward toward the cylinder head end will cause solvent drawn from supply container 75a and stored in the inner chamber 48 to be discharged through the inner outlet 68. When the control valve 80 is moved to position B, axial movement of the drive piston 36 outward toward the cylinder head end will cause solvent drawn from supply container 75b and stored in the outer chamber 49 to be discharged through the outer outlet 73. Thus, solvent flow from two separate supplies can be obtained using one pump controlled by a 2-way control valve.

Herein, if the drive piston 36 moves at a constant rate, the amount of solvent delivered from the pump 30 to the sample injector 82 is controlled by the stepper motor 52 and will be constant regardless from which outlet solvent is discharged. The proportion of solvents delivered is controlled by the control valve 80. For example, if the composition of solvent A to solvent B is to be 75:25, then the time that the valve is at position A is simply 750 milliseconds and the time that the valve at position B is 250 milliseconds. If a 10:90 composition is required, then the valve will be in position A for 100 milliseconds and in position B for 900 milliseconds. The valve continuously switches between A and B with each complete switching cycle taking one second or less. By simply changing of the timing of any mix of A/B, a variety of gradient modes can be easily produced.

To restore the supply of solvent fluid within the pump inner and outer chambers 48 and 49 during a refill cycle, the drive piston 36 during its suction stroke is retracted inward away from the cylinder head end. With the control valve 80 in either position and the floating piston 45 spaced from the first cylinder section, solvent is drawn from supply container 75b into the outer chamber 49 by the action of the tapered spring 62 biasing the floating piston 45 inward. Pressure in the inlet lines from the supply reservoir is higher than the pressure in the cylinder section during retraction of the drive piston 36 so that the pump is reloaded. When the floating piston 45 abuts the head end of the housing 33, continued inward movement of the drive piston 36 away from the head end draws solvent from supply container 75a into the inner chamber 48.

INDUSTRIAL APPLICABILITY

It should be apparent that the gradient pump described herein is a simple, functional unit that is effective and inexpensively manufactured.

The gradient syringe pump design disclosed herein can be simply controlled using only one motor controller and simple control logic to produce constant flow gradient analysis than a two pump design.

The gradient syringe pump design disclosed herein has only one motor and requires less power to drive than a two pump design.

Other aspects, objects and advantages of this invention can be obtained from a study of the drawings and the foregoing disclosure.

It should be understood that the terms "top," "bottom," "forward," "rearward," "first," "second," "upper," "lower," "inner," "outer," "inward," "outward," "end," "side," and similar terms as used herein, have reference only to the structure shown in the drawings and are utilized only to facilitate describing the invention. The terms and expressions employed herein have been used as terms of description and not of limitation.

As used herein, the term "within" shall mean "to be partially or completely inside of"; the term "axial" refers to a direction that is substantially straight; the term "transverse" refers to a direction other than the axial direction (e.g., orthogonal or nonorthogonal); and, the term "fluid" refers to both liquids and gases. From the foregoing, it will be observed that numerous variations and modifications may be effected without departing from the spirit and scope of the invention. It will also be observed that the various elements of the invention may be in any number of combinations, and that all of the combinations are not enumerated here. It will be understood that no limitation with respect to the specific apparatus illustrated herein is intended or should be inferred. While specific embodiments of the invention have been disclosed, one of ordinary skill in the art will recognize that one can modify the materials, dimensions and particulars of the embodiments without straying from the inventive concept.

What is claimed is:

1. A pump for moving fluids comprising:
a housing having a wall, defining an internal cavity closed at one end;
a first piston within said cavity;
a motor for selectively moving said first piston linearly along a pump axis outwardly toward and inwardly away from said one end;
a second piston floating intermediate said one end and said first piston, said second piston being linearly movable along the pump axis and separating the internal cavity into a first pumping chamber and a second pumping chamber, said first piston being disposed within said first pumping chamber;
a first pump inlet and a first pump outlet intermediate said second piston and said first piston communicating with said first pumping chamber;
said first pump inlet and first pump outlet being disposed to remain open to fluid flow with said first pumping chamber at any linear position of said first piston;
a second pump inlet and a second pump outlet intermediate said second piston and said one end communicating with said second pumping chamber;
said second piston movable between a first position toward said first pump inlet and first pump outlet and a second position toward said second pump inlet and second pump outlet;
a spring biasing said second piston axially toward said first piston; and,
a 2-position valve to control fluid flow from the pumping chambers, said valve having first and second valve inlets and a valve outlet, said first valve inlet communicating with said first pump outlet, a said second valve inlet communicating with said second pump outlet, said valve being selectively switchable between a first position opening said first valve inlet allowing fluid flow from said first pumping chamber and shutting off fluid flow from said second pumping chamber and a second position opening said second valve inlet to said valve outlet allowing fluid flow from said second pumping chamber and shutting off fluid flow from said first pumping chamber, and wherein switching said valve between said first and second positions delivers fluid through said valve alternately from said first and second pumping chambers.

2. The pump of claim 1 wherein said housing defines a first cylinder section having a first diameter, said first piston being movable within said first cylinder section, and said housing defines a second cylinder section having a second diameter greater than said first diameter, said second piston being movable within said second cylinder section between said first cylinder section and said closed end.

3. The pump of claim 1 further including a check valve upstream of said first pump inlet preventing backflow from said first pumping chamber and a check valve upstream of said second pump inlet preventing backflow from said second pumping chamber.

4. The pump of claim 1 wherein said spring is a constant force spring disposed between said closed end and said second piston.

5. The pump of claim 4 wherein said constant force spring is a tapered constant force spring.

6. The pump of claim 1 wherein said spring applies a force between 2 and 10 pounds.

7. The pump of claim 1 wherein said second piston has a recess on a side facing said second pumping chamber and said spring is disposed between said closed end and said second piston extending into said recess.

8. The pump of claim 1 wherein said second piston has a recess on a side facing said second pumping chamber, said spring is disposed between said closed end and said second piston extending into said recess, and said recess has a depth enabling said spring to be compressed completely into said recess.

9. The pump of claim 1 wherein said first pump inlet and said first pump outlet extends through said housing wall near the first position of said second piston, and said second pump inlet and said second pump outlet extends through said housing wall near the second position of said second piston.

10. The pump of claim 1 wherein said second piston has an annular groove adjacent its periphery on a side facing said first pumping chamber to define a peripheral skirt radially outward of the groove for sliding engagement with said housing wall.

11. The pump of claim 1 wherein said housing defines a first cylinder section having a first diameter and said first piston is disposed within said first cylinder section, and further including an endcap closing said one end of said housing, said endcap having a transverse end wall and an annular side wall extending axially from said end wall defining a second cylinder section having a second diameter greater than said first diameter, said second piston being disposed within said second cylinder section between said first cylinder section and said closed end.

12. A pump for moving fluids comprising:
a housing having a wall, defining an internal cavity closed at one end;
a first piston within said cavity;
a motor for selectively moving said first piston linearly along a pump axis outwardly toward and inwardly away from said one end;
a second piston floating intermediate said one end and said first piston, said second piston being linearly movable along the pump axis and separating the internal cavity into a first pumping chamber and a second pumping chamber;
said housing defining a first cylinder section having a first diameter, said first piston being movable within said first cylinder section;
said housing defining a second cylinder section having a second diameter greater than said first diameter, said second piston being movable within said second cylinder section between said first cylinder section and said closed end;
a first pump inlet and a first pump outlet intermediate said second piston and said first piston communicating with said first pumping chamber;
said first pump inlet and first pump outlet being disposed to remain open to fluid flow with said first pumping chamber at any linear position of said first piston;
a second pump inlet and a second pump outlet intermediate said second piston and said one end communicating with said second pumping chamber;

said second piston movable between a first position toward said first pump inlet and first pump outlet and a second position toward said second pump inlet and second pump outlet;

a check valve upstream of said first pump inlet preventing backflow from said first pumping chamber and a check valve upstream of said second pump inlet preventing backflow from said second pumping chamber;

a spring biasing said second piston axially toward said first piston; and, a 2-position valve to control fluid flow from the pumping chambers, said valve having first and second valve inlets and a valve outlet, said first valve inlet communicating with said first pump outlet, said second valve inlet communicating with said second pump outlet, said valve being selectively switchable between a first position opening said first valve inlet allowing fluid flow from said first pumping chamber and shutting off fluid flow from said second pumping chamber, and a second position opening said second valve inlet allowing fluid flow from said second pumping chamber and shutting off fluid flow from said first pumping chamber, and wherein switching said valve between said first and second positions delivers fluid through said valve alternately from said first and second pumping chambers.

13. The pump of claim 12 wherein said spring is a constant force spring disposed between said closed end and said second piston.

14. The pump of claim 13 wherein said constant force spring is a tapered constant force spring.

15. The pump of claim 12 wherein said second piston has a recess on a side facing said second pumping chamber, said spring is between said closed end and said second piston extending into said recess, and said recess has a depth enabling said spring to be compressed completely into said recess.

16. The pump of claim 12 wherein said first pump inlet and said first pump outlet extends through said housing wall near the first position of said second piston, and said second pump inlet and said second pump outlet extends through said housing wall near the second position of said second piston.

17. The pump of claim 12 the housing, including an endcap closing said one end of said housing, said endcap having a transverse end wall and an annular side wall extending axially from said end wall defining said second cylinder section.

* * * * *